United States Patent [19]

Quemerais et al.

[11] Patent Number: 4,470,910

[45] Date of Patent: Sep. 11, 1984

[54] CHROMATOGRAPHIC APPARATUS AND PROCESS FOR ITS USE

[75] Inventors: Claude Quemerais, Ermont; Catherine Porho, Les Lilas, both of France

[73] Assignee: Instruments S. A., Paris, France

[21] Appl. No.: 470,027

[22] Filed: Feb. 25, 1983

[30] Foreign Application Priority Data

Feb. 25, 1982 [FR] France .................. 82 03177

[51] Int. Cl.$^3$ ............................................. B01D 15/08
[52] U.S. Cl. .................. 210/656; 210/198.2; 422/70
[58] Field of Search .............. 210/198.2, 656, 659; 422/70

[56] References Cited

U.S. PATENT DOCUMENTS

| | | | |
|---|---|---|---|
| 3,954,617 | 5/1976 | Ishimatsu | 210/198.2 |
| 3,963,614 | 6/1976 | Osawa | 210/198.2 |
| 3,966,609 | 6/1976 | Godbille et al. | 210/198.2 |
| 4,174,772 | 11/1979 | Neuss et al. | 210/198.2 |
| 4,311,586 | 1/1982 | Baldwin et al. | 210/198.2 |
| 4,350,595 | 9/1982 | Gunkel | 210/198.2 |

OTHER PUBLICATIONS

Introduction to Modern Liquid Chromatography by Snyder et al., John Wiley & Sons, pp. 137–139 and 147–149, 1979.
High Performance Liquid Chromatography by Knox., Edinburgh Press of Scotland, p. 185, 1978.

Primary Examiner—John Adee
Attorney, Agent, or Firm—Pollock, Vande Sande & Priddy

[57] ABSTRACT

A liquid-phase preparative chromatographic apparatus comprising a column in the form of a cylindrical tube equipped at its lower section with a cap; a filling device to be connected by means of a compression nozzle and comprising a cylinder for actuating a non-porous solid body that compresses the stationary phase with which the column is filled by means of the compression nozzle; an injection head to be fastened onto the column after it is filled and comprising a lower wall and an injection unit having a diameter smaller than the injection head and equipped with several lateral solute supply ports, the head comprising on its upper surface a central solvent supply port and means enabling the solvent to flow around the injection unit; a pump connected to the injection head and comprising four pistons activated by cams or rods disposed at 90° angles from one another and having a base of support that is not integral with the block; a detection device consisting of a double detection assemblage; and a fraction collector connected to the detection means and comprising two superimposed compartments.

10 Claims, 10 Drawing Figures

CHROMATOGRAPHIC APPARATUS AND PROCESS FOR ITS USE

The present invention relates to a chromatographic apparatus and a process for its use.

The invention relates more specifically to a complete apparatus for pressurized, liquid-phase, preparative chromatography that makes it possible to tackle chromatography of any solid or liquid mixture from the filling of the column through collection of the separated products, whatever the type of chromatography being used: adsorption, partition, ion exchange, or molecular exclusion.

It is known that preparative chromatography presents special problems due to the use of a column with a considerably greater diameter than other chromatographic apparatuses.

Problems are encountered essentially with the efficiency of the column itself, with the method of injecting the solvent and the solute, and with the circulation of the solvent inside the column.

The present invention provides a solution to these problems and makes it possible to improve the performance of the column and its efficiency.

The invention also provides a new solution to the problems of detection and collection posed by this type of chromatography.

Columns were first filled with a dry, stationary phase. They were then tamped or vibrated in an effort to reduce the interstitial volume between the grains of the stationary phase.

Next, it was thought to fill the columns with a wet stationary phase. However, use of such a wet stationary phase presented a disadvantage resulting from the selective decantation of particles as a function of their granulometry. This led users to push the wet stationary phase down with a pressurized fluid. Use of a pressurized fluid, however, has the disadvantage of being dependent on the handlers and gives satisfactory results solely for small-diameter columns.

Also proposed has been the use of either centrifugal or centripetal radial or axial compression to improve the column's efficiency. Thus was suggested the idea of axial compression having to be maintained during chromatography itself. Such an apparatus notably comprises a gas- or liquid-permeable sliding body that applied pressure over the stationary phase inside a tube having at the other end a gas- and liquid-permeable cap that connects with the outside just as the sliding body itself does. However, this type of apparatus has the disadvantage of drying out the stationary phase at the points where pressure is applied by the sliding body. Furthermore, the use of such a sliding body poses problems of leakage of solvents, which are often very corrosive and dangerous.

Lastly, this type of apparatus is applied all through the chromatography, involving expenditures of energy and tending possibly to alter the compactness of the stationary phase during the chromatography operation itself, following introduction of the solvent and solute into the column for separation.

The inventors have discovered means for overcoming such drawbacks through the use of a filling station comparable to the filling station for pressurized analytical columns, with the fundamental difference that the stationary phase is compressed within the tube of the column by a non-porous solid body instead of a liquid.

Because of said means, it is possible to improve the performance of the column considerably by avoiding the disadvantages mentioned above. Among other things, granulometric gradients and the flow of eluates through the piston can be avoided in this way. The efficiency of the column is also considerably improved. This is a very important criterion, since fineness of separation depends on efficiency and on the possibility of separating products according to their variable retention times in the column.

With regard to the injection of liquids, prior processes essentially posed problems of non-homogeneous distribution over the entire surface of the column, resulting from a linear speed gradient of solute and solvent inside the column, and from wall effects that cause the solute migrating within the column to move more quickly along the wall than the solute migrating within the stationary phase.

The present invention is also designed to cure this problem through use of a column that has been filled by the filling station defined above and through use of an injection head having means for forming a tube of solvent along the wall and means for injecting the solute laterally in such a way that the streams collide radially and diffuse uniformly through the head.

With regard to the circulation of the solvent, the most important problem has been the pulsing of the pump. The inventors solved this problem by employing a four piston, 90°, cam- or rod-activated pump giving a perfectly linear and completely stabilized output for a given uniform speed of rotation of the cam-shaft.

These various means, in combination, enable considerable improvements in the efficiency and precision of separation of the chromatographic column to be made.

In addition to the means set forth hereinabove, the applicant has also perfected means for improving the detection and collection of the fractions.

The object of the present invention is therefore a chromatographic apparatus with improved efficiency.

Another object of the invention consists of a process for using said apparatus in the course of pressurized, liquid-phase, preparative chromatography.

The apparatus of the invention comprises at least one filling device comprising (i) the column, in the form of a cylindrical tube, equipped at its bottom with a cap having a disk that stops solid particles while allowing liquids and gases to pass through, connected to a compression nozzle whose minimum height is equal to a third of the height of the column, and (ii) a cylinder actuating a non-porous solid body that compresses the stationary phase through the compression nozzle.

The non-porous solid body may be actuated by an hydraulic, pneumatic, or screw-type cylinder, or by any other type of cylinder known in the art.

The column is fastened to the cylinder by means of the compression nozzle. It is preferentially made of stainless steel or any other substance usable in this domain.

Once the column is compressed, it is disconnected from the compression nozzle in order to be integrated into the chromatographic system.

The chromatographic apparatus thus described is preferentially connected (after moving to the filling station) to an injection head located in an upper cap which is fastened to the top of the column after the latter has been disconnected from the compression nozzle.

The injection head comprises (i) a lower wall consisting of a plate filled with cells which may or may not be contiguous, associated with a disk of fritted balls made of stainless steel or another substance disposed under the cell-filled plate, and (ii) an injection unit having a diameter smaller than the injection head and equipped with several lateral solute supply ports which cause a radial dispersion of the solute within the injection unit. The upper surface of said injection head comprises a central solvent supply port and means enabling the solvent to flow around the injection head so as to enable the solvent to form a flow all along the inner wall of the column.

In a preferred embodiment, the injection unit comprises at least six lateral ports.

The injection head preferentially has a ratio of diametric area of the central port to diametric area of the lateral ports proportional to the area of the ring formed between the diameter of the column and the diameter of the injection unit to the diameter of the injection unit.

The injection head is, according to the invention, connected to a pump that comprises four pistons activated by cams or rods arranged at 90° to one another, whose support base is not integral with the block comprising the four pump heads, said block comprising four pump heads each equipped with a suction valve and a delivery valve not integral with the motor-cam shaft support.

Said block is preferentially disposed on slides and may be translated along a distance equal to the depth of a pump head chamber by means of a vernier, which may be graduated in milliliters.

In accordance with the invention, each of the four chambers of the pump heads is successively compressed, which has the effect of giving a perfectly linear and completely stabilized output for a given speed of rotation of the cam shaft (which may be 1 rev/sec.).

The detection means that enable the performance of the chromatographic column to be improved still further involve a double detection set-up using absorptiometry and refractometry over a single tank comprising a detection tank subjected to perpendicular infrared and ultraviolet radiation in one or more planes.

The detection tank comprises four polished surfaces—two of which are infra-red quality quartz and two ultraviolet quality quartz—and a low voltage double detection block, with the high voltage of the lamp that is the source of the u.v. radiation being sent outward by means of optical fibers.

The inventors observed that double detection often poses problems due to the fact that the solvent compressed by the pump circulates within the column under high pressure before reaching the u.v. detection tank. Leaving the tank, the solvent expands and bubbles can be observed to form, disturbing refractometric detection. If the order of detection is reversed, gas removal in the u.v. tank does not inhibit detection, but the pressure variations entailed by this gas removal disturb the refractometric detection taking place upstream and considerable background noise appears.

The above-described double detection arrangement using a single tank therefore consists essentially of measuring the refraction index difference from a low voltage infrared source on a known refractometric apparatus with a double circulation tank (sample and control). The arrangement of the invention was made using u.v. sources, i.e., directly upon the output of a holographic lattice monochromator. The radiation is picked up in a UV 200 QSF fiber approximately two meters or more in length and directed into the tank perpendicular to the infra-red rays and in a different plane. By using a fiber with, for example, a numerical opening of 0.4 and a lens system with focal distances of, for example, 2.3 mm, the parallel radiation is rendered across the tank and then made to reconverge toward, for example, a UV 1000 QSF fiber in order for the radiation to be sent toward a conventional photo-multiplier.

Lastly, the inventors have improved the collection of fractions from the point of view of efficiency and safety. No fraction collector with a non-electrical mechanism presently exists. From pump to fraction collector, passing through injection, column, and detection, the solvent is enclosed in tubes and sealed chambers, whereas at the collector it is poured into containers and can expand and give off gases, thereby producing a combustible (deflagrant) atmosphere. Furthermore, if the mechanism breaks down, the containers can overflow and flood the electrical components, which are often located under the container.

The object of the invention is therefore an entirely pneumatic, easy-to-use, and inexpensive fraction collector. This collector comprises two compartments. In the lower compartment a cylinder uses reciprocal motion to actuate a shaft on which two rotationally opposite ratchets are placed for the purpose of unidirectionally driving a pulley equipped with a belt at a fixed angle of rotation. The center of the upper compartment is preferably provided with a hollow shaft driven by the above-described belt, while the compartment itself is equipped with a revolving pneumatic fed coupling. This feed enables the cylinder located on the upper part of the hollow shaft and perpendicular to it to place the solvent capillary opposite the container or opposite an evacuation tank.

An embodiment of a chromatographic apparatus according to the invention will be described below. FIG. 10 is a schematic representation of the process for using the above-described chromatographic apparatus. After putting column C together at filling station PR, the solvent is sent by pump P through column C, then enters detection tank D and flows into fraction collectors CF.

Other features of the invention will become apparent from the following description of an embodiment given by way of example and represented in the attached drawings, in which.

Figure 6:
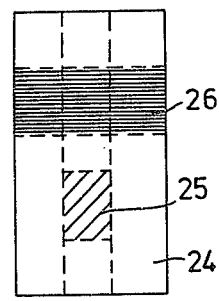
Figure 7:
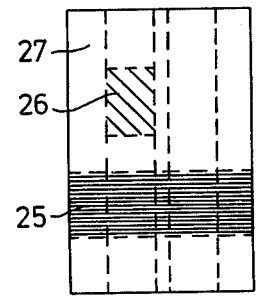
Figure 8:
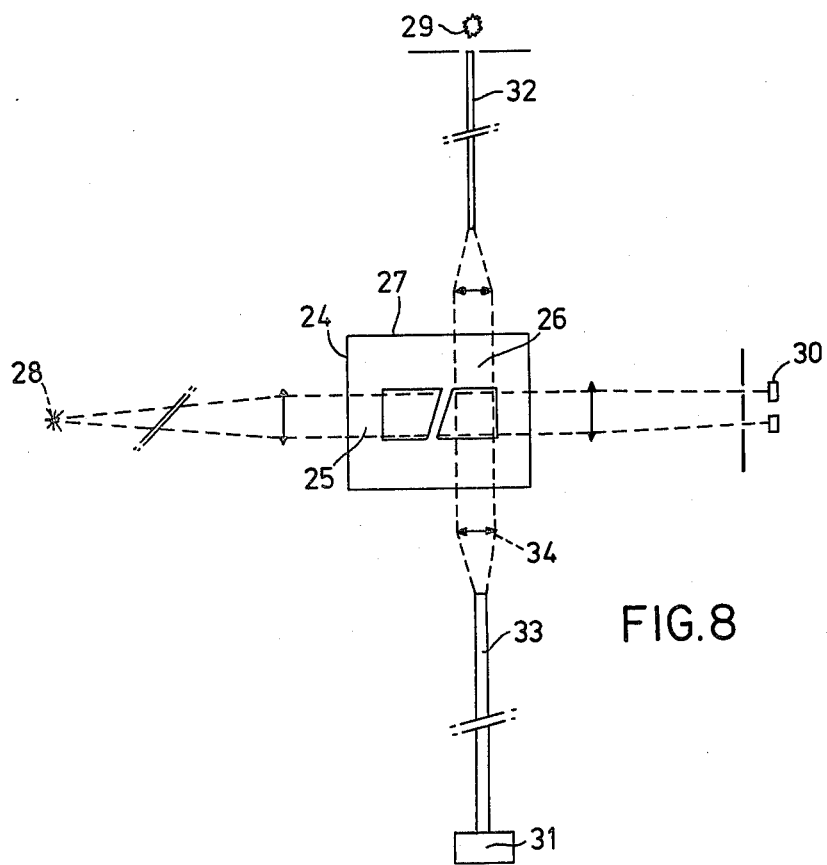
Figure 9:
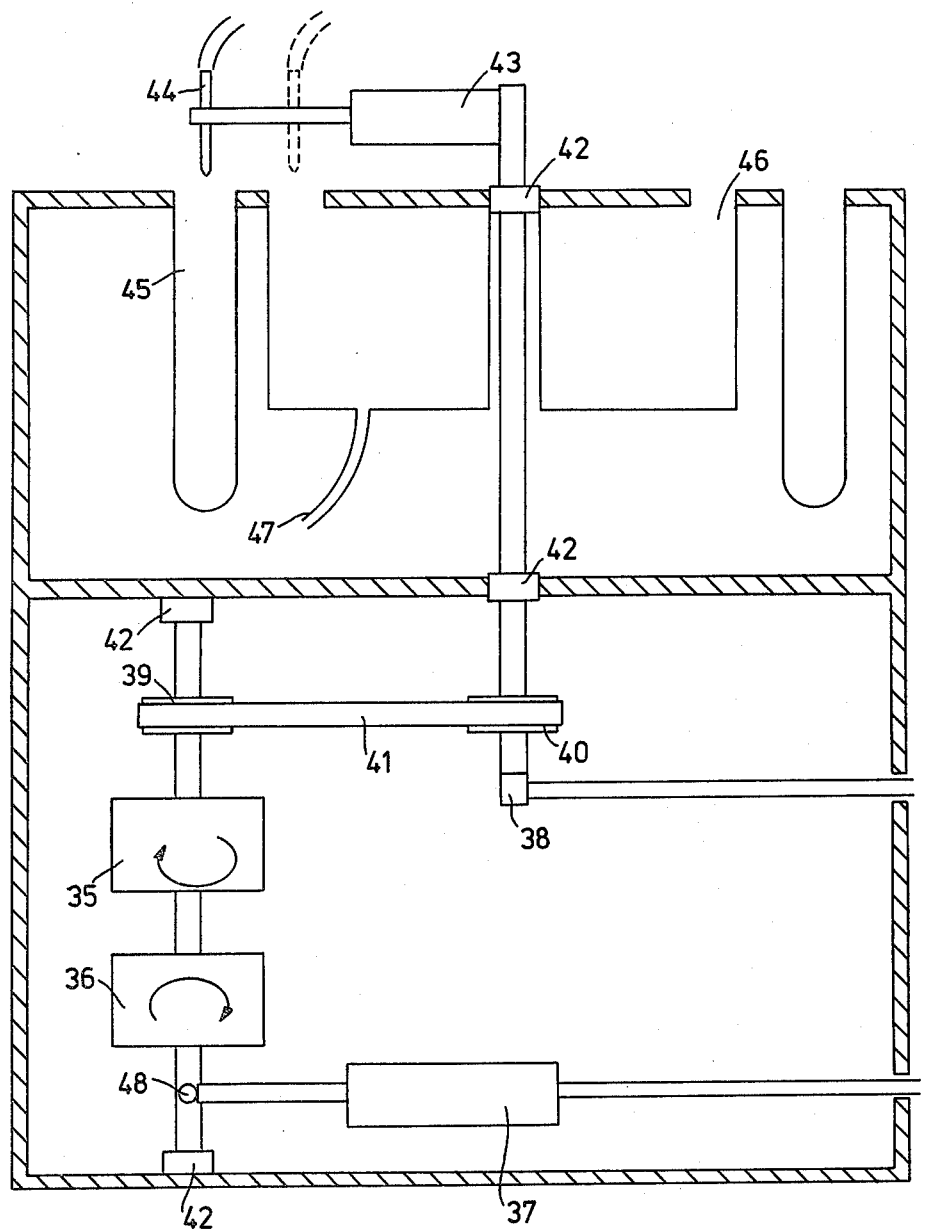

FIGS. 6, 7, and 8 are schematic views of the single, double-detection (absorptiometry and refractometry) tank respectively in front view, side view and top view;

FIG. 9, P, PR, CF are schematic section and projections of the anti-deflagrant pneumatic fraction collector.

Figure 10:
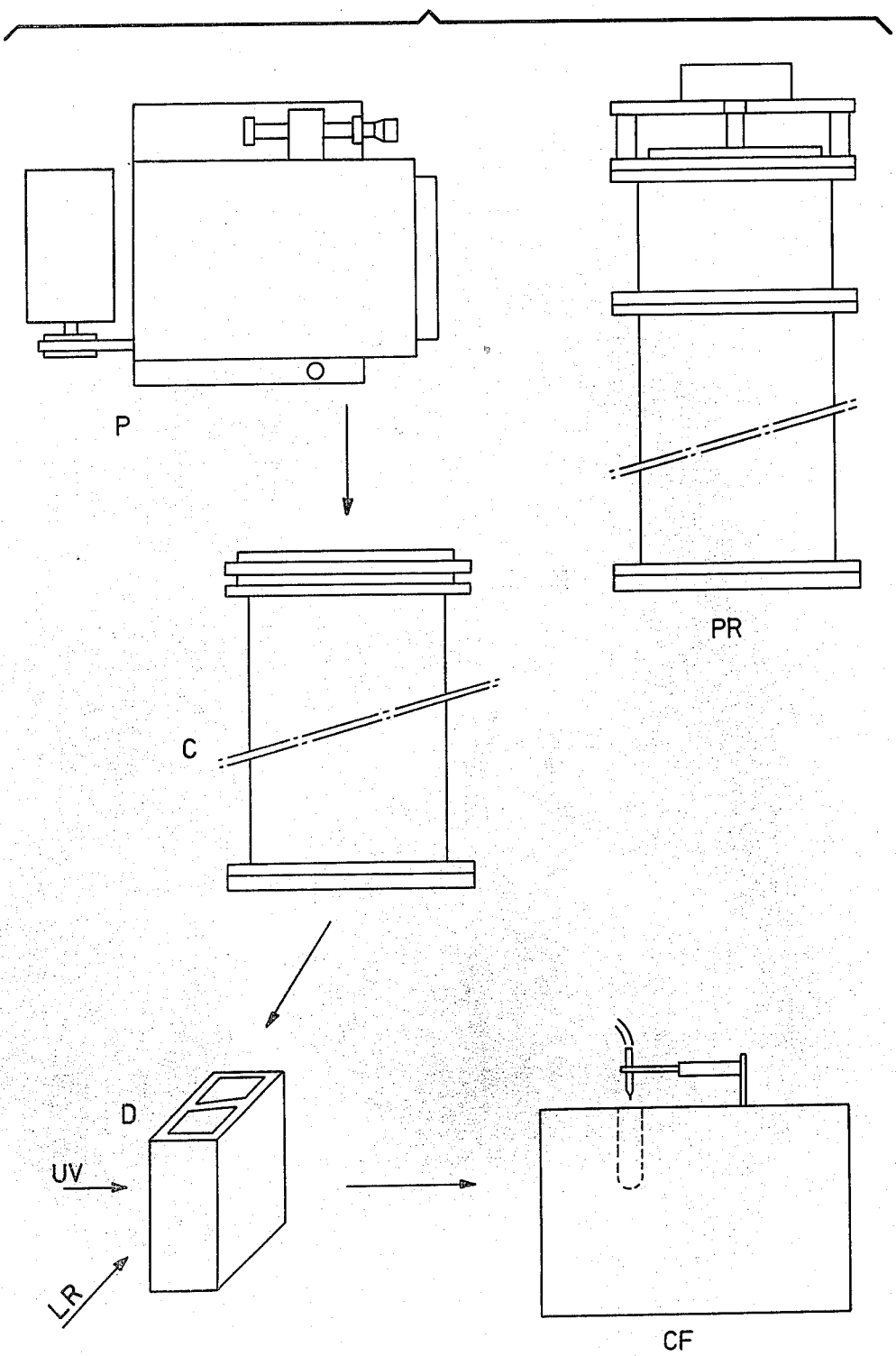

FIG. 10 shows a pneumatic, hydraulic, screw-type or other cylinder 1 fastened to filling nozzle 4 by a clamp 2. Cylinder 1 actuates the non-porous solid body 3 inside filling nozzle 4.

The stroke of cylinder 1 is less than or equal to the length of filling nozzle 4. The column to be filled with the stationary phase 5 is equipped with a lower cap 8 (equipped with a cell-filled plate 7 for recovery of solutes) directly surmounted by a disk of fritted balls 6, preferentially of stainless steel. The tightness of the seal at the connection between filling nozzle 4 and the column and between column 5 and cap 6 is assued by means of flat gaskets, which may be teflon.

Figure 1:
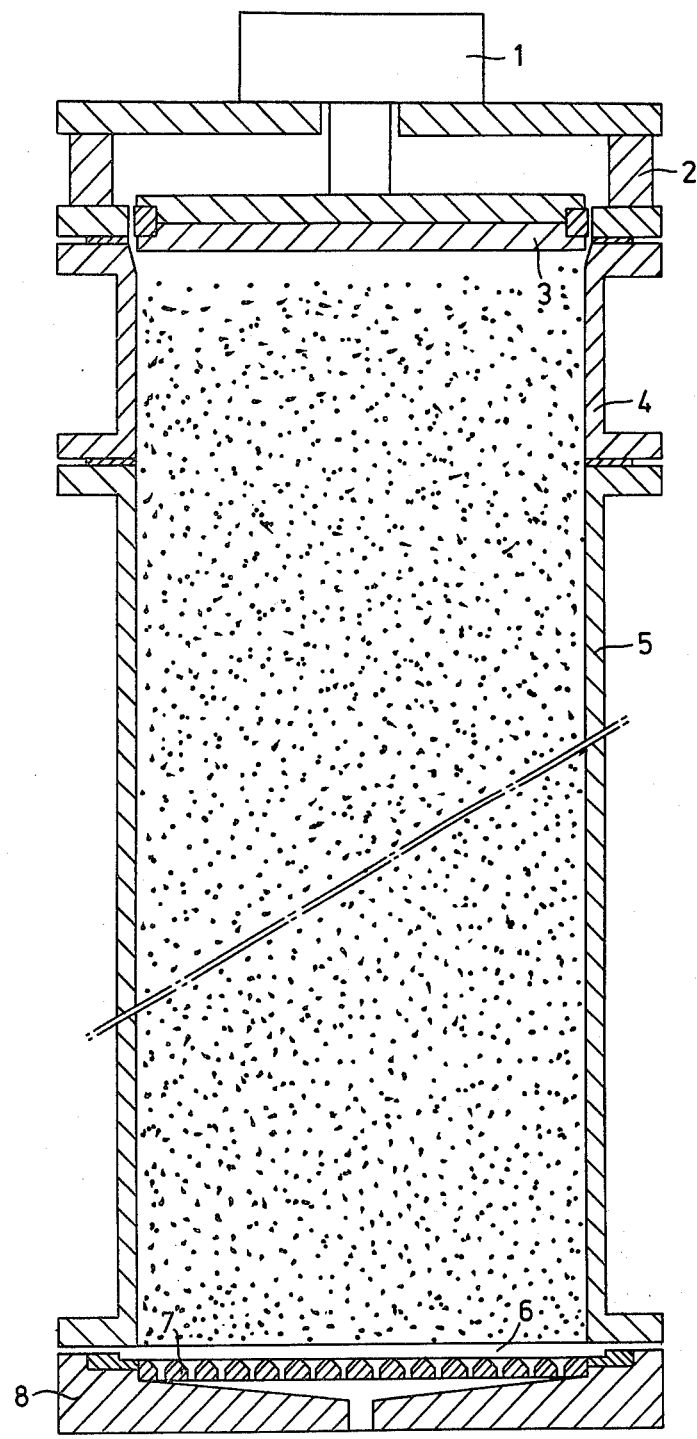
FIG. 1 is a schematic section of the filling station of the preparative, liquid-phase chromatographic column.
Figure 2:
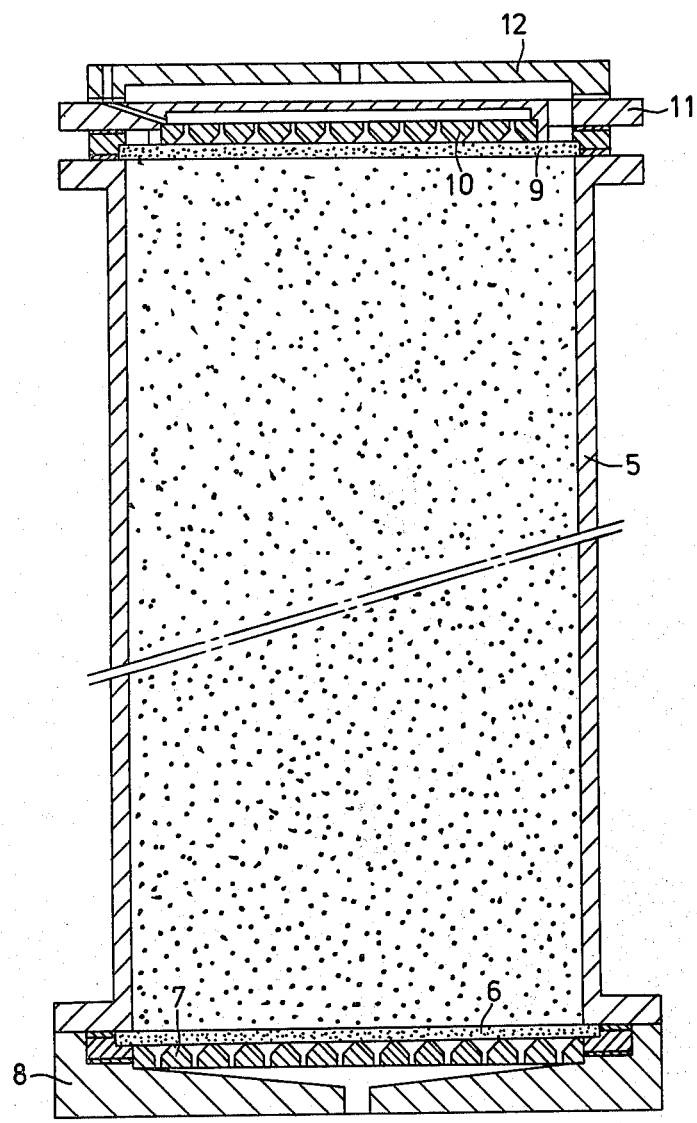
FIG. 2 is a schematic section of the preparative column after having been disconnected from the filling station and equipped with the injection head.

In FIG. 2, column 5 is disconnected from injection nozzle 4 represented in FIG. 1 and in place of said nozzle has upper cap 12 equipped with injection unit 11 inside which lies cell-filled distributor plate 10, directly above disk 9 of fritted balls. The tightness of the seal at the connection between upper cap 12 and injection unit 11 and between injection unit 11 and column 5 is assured by means of flat gaskets, which may be teflon.

Figure 3:
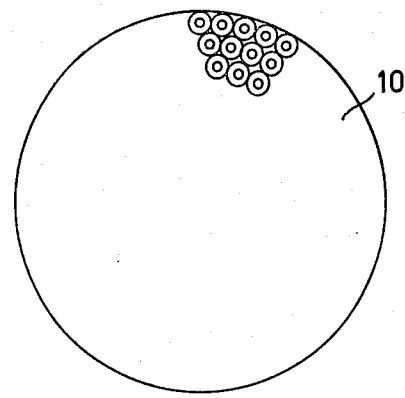
FIG. 3 is a schematic projection of the cell-filled plate.

In FIG. 3, cell-filled plate 10 is set of double-coned holes forming cells which may or may not be contiguous.

Figure 4:
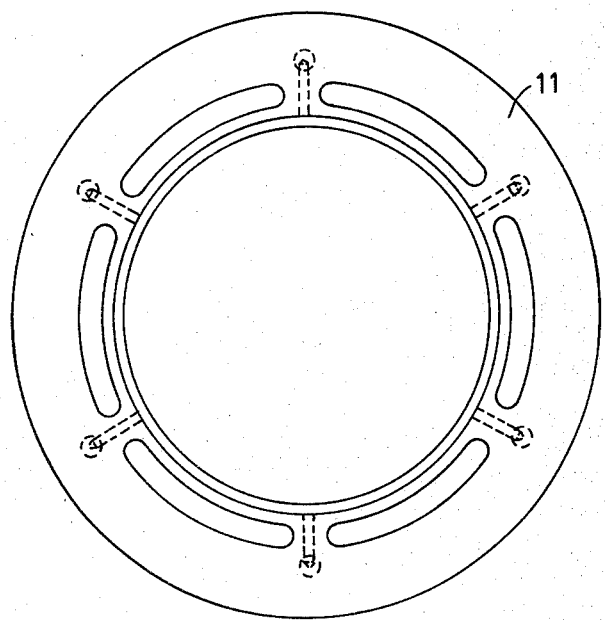
FIG. 4 is a schematic projection of the injection unit and the lateral supply ports.

In FIG. 4, injection unit 11 is represented without its cell plate. The six holes shown in dotted lines represent the six lateral supply ports that irrigate the cell plate. Between these six holes are represented the six bean-shaped zones irrigated by the central solvent port situated over upper cap 12 so as to form a tube of solvent that coats the column from within.

Figure 5:
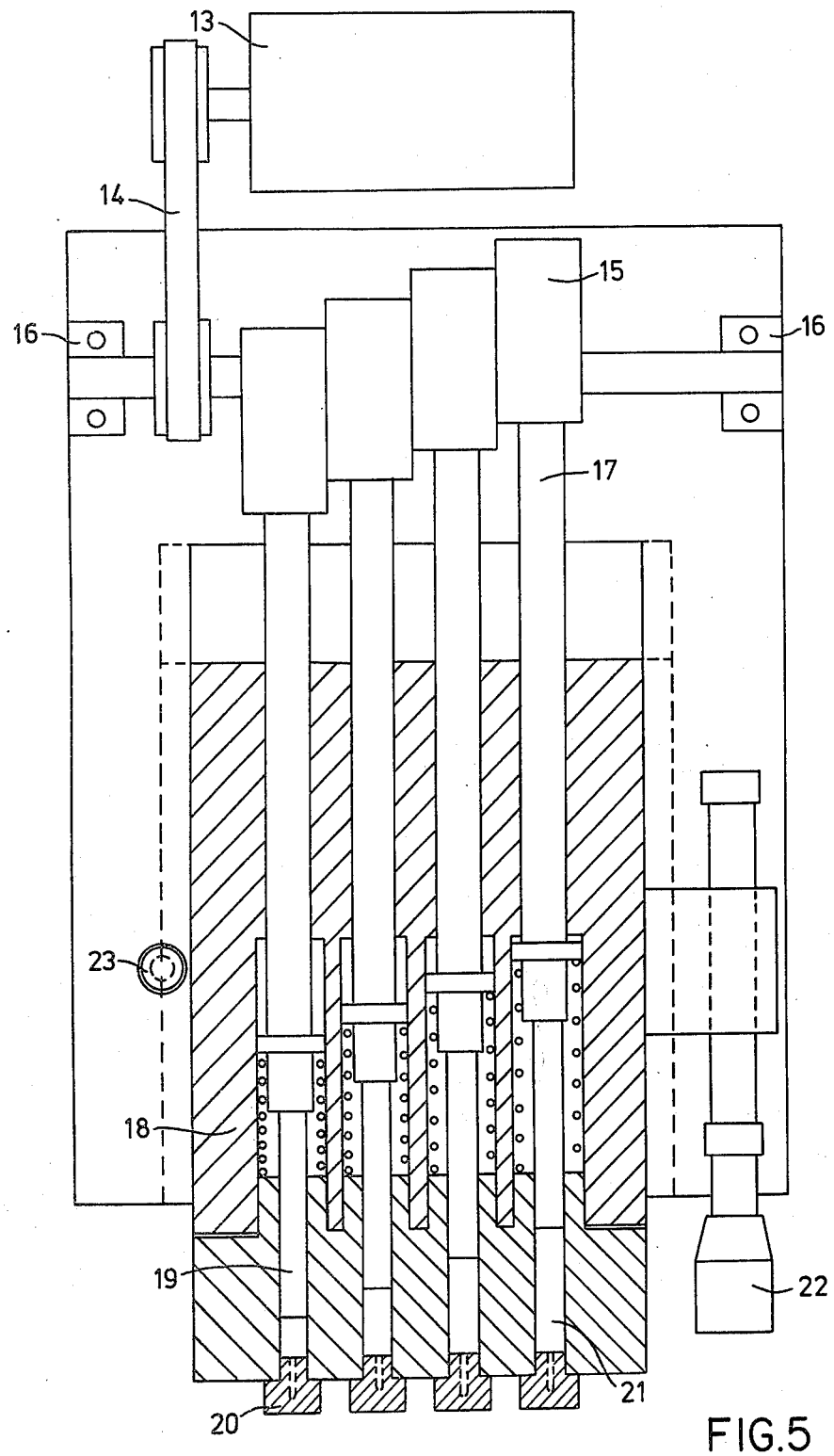
FIG. 5 is a schematic section and projection of the four-piston pump for liquid-phase chromtography.

FIG. 5 represents the four-piston chromatographic pump, the output of which is adjustable during operation. A motor 13 that may be electric or pneumatic uses belt 14 to drive cam shaft 15, which is affixed to bearings 16.

Drive pistons 17 are not integral with the cams, thus making it possible to adjust their stroke with reference to the pump frame. Compression pistons 19 are integral with drive pistons 17 and are equipped with return springs 18.

The solvent is compressed within compression chamber 21 by compression piston 19. Solvent enters and leaves compression chamber 21 through double suction-delivery valve 20. The hatched portion of FIG. 5 representing the pump piston and head block can be translated with respect to the non-hatched portion representing the motor and cam shaft block by a distance equal in length to the depth of the compression chamber 21 by means of vernier 22. A screw 23 for blocking the slides of the block enables the assembly to lend rigidity to the adjustment system.

In FIGS. 6, 7, and 8, reference 24 represents the front surface of the detection tank, and reference 27 the side surface. Reference 25 represents the optical path of the infra-red rays used for refractometric detection. Reference 26 is the optical path of the u.v. rays used for absorptiometric detection. Reference 28 denotes the infra-red source and reference 30 the detection cells. Reference 29 is the u.v. source and 31 the detection photomultiplier. The u.v. rays travel through an optical fiber 32 that may be 200 microns or more in diameter and cross the tank in parallel radiation from a lens system 34 before reconverging toward an optical fiber 33 that may have a diameter of 1,000 microns or more.

FIG. 9 represents the completely pneumatic and antideflagrant fraction collector. Single-action pneumatic cylinder 37 uses reciprocal motion to actuate pin 48 along an angle of rotation that is adjustable from the stroke of cylinder 37. This reciprocal motion of pin 48, located on the shaft affixed to the frame by ball bearings 42, produces a simple rocking of ratchet 36 but a point-by-point and unidirectional rotation of the second, oppositely placed ratchet 35. This rotation is transmitted to pulley 39 and then to pulley 40 through belt 41.

Pulley 40 rotates a hollow shaft affixed to the frame by ball bearings 42. This hollow shaft is supplied with pressure through a revolving coupling 38 so as to actuate cylinder 43, which positions the flow of solvent 44 above collection container 45 or above an evacuation vat 46. Evacuation vat 46 is equipped with an evacuation tube 47.

A process for using the chromatographic apparatus of the invention will now be described. Lower cap 8 has been affixed to column 5. Onto the upper part of the column, injection nozzle 4 is fastened. This assembly is then filled with the stationary phase in suspension, e.g., in the elution solvent.

Cylinder 1 with its clamp 2 is fastened onto injection nozzle 4. Non-porous solid body 3 is at this time in raised position. Cylinder 1 actuates non-porous solid body 3, causing it to descend into injection nozzle 4 and compress the stationary phase. Non-porous solid body 3 is then in lowered position. This lowered position is still inside the body of the injection nozzle. It is never inside column 5 since its lower limit lies at the base of injection nozzle 4, i.e., at the upper part of column 5. The compression of the stationary phase is a function of the diameter of the particles, but also of the specific and physical characteristics of the various stationary phases. A cellulose cannot be compressed in the same manner as a silica.

Once compression is achieved, the pressure exerted by cylinder 1 is stopped, column 5 is disconnected from injection nozzle 4, and injection head 12 and 11 is fastened to column 5. Column C is then integrated into the chromatographic system.

The four pump heads 20 of pump P are connected to the injection head by a combination of stainless steel three- or four-way valves to make it possible to change the solvent or to elute the column in the upward direction. One of the four pump heads is connected to the central supply port of cap 12 while the other three are connected to the lateral ports.

On the suction side, these three pump heads are each equipped with a three-way valve that makes it possible to take in either solvent or the solute to be injected. During elution, the four pump heads deliver solvent over the injection head through the central and lateral supply ports. During injection, the central port is always supplied with solvent while the lateral ports are being supplied with solute. There is therefore no variation of flow during injecton. Most important, injection is not done in "stop/flow" fashion, thereby totally eliminating harmful pressure surges at the moment of injection.

Of course, in an automated version the use of such a system is extremely simple since it is limited to turning the three-way valves rather than stopping the pump for the injection and then starting it up again.

Such an application clearly demonstrates the savings achieved over existing systems. In fact, instead of having one system for elution and one for injection, the two are combined in one by virtue of the four pump heads.

After passing through column C, the eluant is directed toward double-detection tank D and then toward fraction collector CF. Advantageously, valves are disposed between D and CF for recycling the solute or recycling the solvent toward the pumping reservoir. These valves can be activated as a function of instructions given by the detection tank. For example, if the solutes are perfectly separated, the valves are not activated and the eluant goes into the collector. If the solutes are badly separated, the solute recycling valve is activated and the eluant is returned to the top of the column. Finally, if the detection tank gives not instruction, the solvent recycling valve is activated (and) the eluant is sent back toward the pumping reservoir.

When separation of the solutes is deemed satisfactory, the eluant is sent toward the collector where, by means of cylinder 37, the solute is distributed into the various collection containers. The areas between two solutes or the ends of solutes are sent to evacuation vat 46 by means of cylinder 43.

We claim:

1. Liquid-phase preparative chromatographic apparatus comprising at least one filling device comprising
    (a) a chromatographic column in the shape of a cylindrical tube;
    (b) a cap at the lower end of said tube comprising a disk that prevents the passage of solid particles while permitting the passage of fluids;
    (c) a compression nozzle detachably connected to said column and having a height at least one-third of the latter;
    (d) an injection head for connection to said column after detachment of said compression nozzle from said column; and
    (e) a cylinder for actuating a non-porous solid body that compresses a stationary phase through said compression nozzle.

2. Apparatus according to claim 1, wherein said injection head is located in an upper cap and comprises a lower wall consisting of a plate filled with cells jointed to a disk of fritted balls disposed beneath said plate, and an injected unit having a diameter less than that of said injection head and having a plurality of lateral solute supply ports causing radial dispersion of solute within said injection unit above said plate, an upper surface of said injection head having a central solvent supply port and said injection head itself having means enabling said solvent to flow around said injection head so that said solvent forms a film along the inner wall of said column.

3. Apparatus according to claim 2, wherein the ratio of the cross sections of said central solvent supply port and said lateral solute supply ports is proportional to the area between the diameters of said column and said injection unit to the diameter of the latter.

4. Liquid-phase chromatographic apparatus having a chromatographic column connected to an injection head which is in turn connected to a pump comprising four pistons actuated by cams or rods disposed at 90° to one another, and further comprising a block, not integral with the supporting base of said pump, comprising four pump heads each having a suction valve and a delivery valve not integral with the support for the motor/cam shaft.

5. Apparatus according to claim 4, wherein said block rests on slide means for translation movement along a distance equal in length to the depth of a chamber of said pump head.

6. Chromatographic apparatus comprising at least one detection device consisting of a double detection arrangement using absorptiometry and refractometry on a single detection tank subjected to mutually perpendicular infra-red and ultraviolet radiation, said detection tank having four polished surfaces of which two are made of infra-red quality quartz and two of ultraviolet quality quartz, and a low voltage double detection block, with the high voltage of the ultraviolet radiation lamp being transmitted outwardly by optical fiber means.

7. Chromatographic apparatus comprising a fraction collector connected to a detection device, said apparatus comprising two superimposed compartments the lower of which comprises a cylinder that uses reciprocal motion to actuate a shaft having two rotationally opposite ratchets and driving a belt-equipped pulley in unidirectional rotation along a fixed angle, and the upper of which comprises a shaft connected through said belt to said pulley, with the latter being equipped with a revolving pneumatic supply coupling.

8. Chromatographic apparatus comprising a column in the form of a cylindrical tube equipped at its lower end with a cap comprising a disk that prevents the passage of solid particles while permitting the passage of liquids and gases, said apparatus comprising
    (a) filling means for connection to said column through a compression nozzle the minimum height of which is equal to one-third the height of said column and comprising a cylinder actuating a non-porous solid body that enables compression of a stationary phase filling said column through said compression nozzle;
    (b) an injection head for attachment to said column after filling, said injection head comprising a lower wall consisting of a plate filled with cells associated with a disk of fritted balls disposed under said plate and an injection unit having a diameter smaller than that of said injection head and equipped with a plurality of lateral solute supply ports that produce radial dispersion of a solute within said injection unit located above said plate, said injection head comprising on its upper surface a central solvent supply port and means enabling solvent to flow around said injection unit so that it forms a film along the inner wall of said column;
    (c) a pump connected to said injection head and comprising four pistons actuated by actuation means disposed at 90° angles to each other and having a base of support that is not integral with a block comprising four pump heads, each equipped with a suction valve and a delivery valve not integral with said actuation means;
    (d) a detection device consisting of a double detection assemblage (absorptiometry and refractometry) over a single detection tank subjected to infra-red and ultraviolet rays in perpendicular relation; and
    (e) a fraction collector connected to said detection device and comprising two superimposed compartments the lower of which comprises a cylinder using reciprocal motion to actuate a shaft comprising two rotationally opposite ratchets and driving a belt-equipped pulley unidirectionally along a fixed angle, while the upper compartment comprises a shaft connected through said belt to said pulley, with the latter being equipped with a revolving pneumatic supply coupling.

9. Process for using liquid-phase preparative chromatography, comprising the steps of
    (a) affixing a column in the form of a cylindrical tube, the lower part of which is equipped with a cap comprising a disk that prevents the passage of solid particles while permitting the passage of liquids and gasses to a filling station comprising a compression nozzle the minimum height of which is equal to a one-third the height of said column, and a cylinder actuating a non-porous solid body;
(b) compressing a stationary phase by means of said compression nozzle in such a way that said non-porous solid body, in lowered position, still lies within the barrel of said injection nozzle;
(c) stopping said compression and disconnecting said column from said injection nozzle;
(d) fastening said injection head onto said column, with said injection head comprising a lower wall consisting of a plate filled with cells associated with a disk of fritted balls disposed under said plate and an injection unit having a diameter smaller than said injection head and equipped with several lateral solute supply ports and having on its upper surface a central solvent supply port and means for enabling the solvent to flow around said injection unit;
(e) connecting said injection head to a pump comprising four pistons (19) activated by cams or rods (14) positioned 90° from each other, one of four pump heads being connected to said central supply port of said injection head and the three others to said lateral ports;
(f) using said pump to inject solvent through said central supply port, with said solvent flowing around said injection unit and forming a tube of solvent along the inner wall of said column; and
(g) injecting solute through said lateral supply ports so as to be dispersed radially within said injection unit, spread uniformly over said plate, and diffused through said disk of fritted balls.

10. Process of claim 9, wherein after passing through said column, the eluant is directed onto a detection tank and then toward a fraction collector.

* * * * *